US012797054B2

(12) United States Patent
Calvo et al.

(10) Patent No.: US 12,797,054 B2
(45) Date of Patent: Nov. 17, 2026

(54) MEDICAL SYSTEMS, DEVICES, AND RELATED METHODS FOR LIFTING TISSUE

(71) Applicant: Boston Scientific Scimed, Inc., Maple Grove, MN (US)

(72) Inventors: Yeison Calvo, San Ramón (CR); Barry Weitzner, Acton, MA (US); Juan Pablo Ortiz Garcia, Heredia (CR); Jimena Cespedes Berrocal, Alajuela (CR); Gian Franco Loo Fuchs, San Jose (CR); Julian Fuentes Castro, La Unión (CR); Cristian Araya Camacho, Tambor (CR); Pablo Montero Rodriguez, La Unión (CR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 306 days.

(21) Appl. No.: 18/426,466

(22) Filed: Jan. 30, 2024

(65) Prior Publication Data

US 2024/0260952 A1 Aug. 8, 2024

Related U.S. Application Data

(60) Provisional application No. 63/482,826, filed on Feb. 2, 2023.

(51) Int. Cl.

| | |
|---|---|
| ***A61B 17/00*** | (2006.01) |
| ***A61B 17/122*** | (2006.01) |
| ***A61B 17/221*** | (2006.01) |
| ***A61B 17/3205*** | (2006.01) |

(52) U.S. Cl.
CPC ...... *A61B 17/00234* (2013.01); *A61B 17/122* (2013.01); *A61B 17/221* (2013.01); *A61B 17/32056* (2013.01); *A61B 2017/00269* (2013.01); *A61B 2017/2212* (2013.01)

(58) Field of Classification Search
CPC ................ A61B 17/122; A61B 17/221; A61B 17/32056; A61B 2017/2212; A61B 17/00234; A61B 2017/00269; A61B 17/0218; A61B 2017/0034
See application file for complete search history.

(56) References Cited

U.S. PATENT DOCUMENTS 10,849,683 B2 12/2020 Weitzner
2004/0102830 A1* 5/2004 Williams ............ A61N 1/0573 607/125

(Continued)

*Primary Examiner* — Andrew Restaino
(74) *Attorney, Agent, or Firm* — Bookoff McAndrews, PLLC

(57) ABSTRACT

A medical system includes an insertion device having a working channel, a first medical device, and a second medical device. The first medical device includes a handle, a sheath extending from the handle and defining a lumen, a helical coil, and a loop. The helical coil is axially and rotatably movable relative to the sheath. A first portion of the loop is coupled to the sheath and a second portion of the loop extends radially away from the sheath. The second medical device is configured to be disposed within the working channel of the insertion device. The second medical device is configured to receive the second portion of the loop. The second medical device is configured to couple the second portion of the loop to a portion of a treatment site.

14 Claims, 7 Drawing Sheets

(56) References Cited

U.S. PATENT DOCUMENTS

| | | | | |
|---|---|---|---|---|
| 2005/0119671 | A1* | 6/2005 | Reydel ............... | A61B 17/0625<br>606/139 |
| 2010/0016659 | A1* | 1/2010 | Weitzner ................ | A61B 34/72<br>600/113 |
| 2018/0235604 | A1* | 8/2018 | Comee ............... | A61B 17/0469 |
| 2019/0029706 | A1 | 1/2019 | Piraka | |
| 2021/0128126 | A1* | 5/2021 | Windheuser ..... | A61B 17/00234 |

* cited by examiner

MEDICAL SYSTEMS, DEVICES, AND RELATED METHODS FOR LIFTING TISSUE

CROSS-REFERENCE TO RELATED APPLICATIONS

This application claims the benefit of priority of U.S. Provisional Patent Application No. 63/482,826, filed on Feb. 2, 2023, the entirety of which is incorporated herein by reference.

TECHNICAL FIELD

This disclosure generally relates to medical systems, devices, and related methods that may be used to treat a subject. More particularly, at least some embodiments of the present disclosure relate to systems, devices, and related methods for lifting tissue.

BACKGROUND

Organ walls are often composed of several layers: the mucosa (the surface layer), the submucosa, the muscularis (muscle layer), and the serosa (connective tissue layer). In gastrointestinal, colonic, and esophageal cancer, lesions or cancerous masses may form along the mucosa and often extend into the lumens of the organs. Conventionally, the condition is treated by cutting out a portion of the affected organ wall. This procedure, however, may cause discomfort to patients, and/or pose health risks.

Physicians have adopted minimally invasive techniques, such as endoscopic procedures like endoscopic mucosal resection (EMR) and endoscopic submucosal dissection (ESD). EMR methods are typically used for removal of small cancerous or abnormal tissues (e.g., polyps), and ESD methods are typically used for en bloc removal of large cancerous or abnormal tissues (e.g., lesions). These procedures are generally performed with an endoscope and other instruments. During these procedures, the endoscope may be passed through a percutaneous incision, passed down the throat, or guided through the rectum to reach tissue targeted for resection or dissection, such a tissue having an abnormality such as a lesion or cancerous mass in an affected organ. The abnormality is generally identified and marked.

The mucosal layer containing the abnormality is then separated from the underlying tissue layers using a medical instrument extending through a working channel, or a lumen, of the endoscope. The abnormality is subsequently removed using the same or different medical instrument. Conventionally, tissue is removed by employing a cutting device such as a wire loop or knife, which may be adapted for electrocautery. Subsequently, excised tissue may be extracted for examination or disposal using a tissue removal device, such as a grasper or other device for holding tissue. Both the cutting device and tissue removal device often need to apply a large traction force or lifting force on the tissue during the procedure, and such a lifting force may be limited by conventional devices. The limited lifting force in conventional tissue cutting and grasping devices may cause increased procedure time, patient injury, or other procedural complications.

The systems, devices, and methods of this disclosure may rectify some of the deficiencies described above or address other aspects of the art.

SUMMARY

Examples of this disclosure relate to, among other things, systems, devices, and methods for performing one or more medical procedures with the medical devices. Specifically, this disclosure includes medical systems and devices comprising an end effector and methods of use thereof (e.g., methods of delivering the end effector to a treatment site of a patient, for example, to lift tissue). Each of the examples disclosed herein may include one or more of the features described in connection with any of the other disclosed examples.

According to one aspect, a medical system may include an insertion device having a working channel, a first medical device, and a second medical device. The first medical device may include a handle, a sheath extending from the handle and defining a lumen, a helical coil, and a loop. The helical coil may be axially and rotatably movable relative to the sheath. A first portion of the loop may be coupled to the sheath, and a second portion of the loop may extend radially away from the sheath. The second medical device may be configured to be disposed within the working channel of the insertion device. The second medical device may be configured to receive the second portion of the loop. The second medical device may be configured to couple the second portion of the loop to a portion of a treatment site.

The medical system may include one or more of the following features. A distal end of the helical coil may be sharpened. In some configurations, the handle may include a stationary body, a first actuator, and a second actuator. The first actuator may control axial movement of the helical coil. The second actuator may control rotational movement of the helical coil. A control element may couple the first actuator and the second actuator to the helical coil. The stationary body may include a first indicator to identify axial movement of the helical coil. The second actuator may include a second indicator to identify the rotational movement of the helical coil. Rotation of the helical coil in a first direction may couple the helical coil to a tissue wall. The tissue wall may be opposite of the treatment site. In some configurations, rotation of the helical coil in a second direction may uncouple the helical coil from the tissue wall.

In some configurations, the helical coil may include a plurality of windings. Adjacent windings of a first portion of the plurality of windings may be spaced by a first distance. Adjacent windings of a second portion of the plurality of windings may be spaced by a second distance. Adjacent windings of a third portion of the plurality of windings may be spaced by a third distance. In some configurations, the third distance may be greater than the second distance. The second distance may be greater than the first distance.

In some configurations, the second medical device may include a clip. The medical system may further comprise a coupler. The coupler may couple the first medical device to an external surface of the insertion device. The second portion of the loop may be comprised of a resilient material.

In some configurations, the medical system may further include a third medical device. The third medical device may be configured to be disposed within the working channel of the insertion device. The third medical device may be configured to cut tissue. The insertion device may be a scope. A distal portion of the scope may be deflectable. The insertion device may include one or more visualization devices.

According to an alternative embodiment, a medical device may include a handle, a sheath extending from the handle and defining a first lumen, a helical coil, and a loop. At least a portion of the helical coil may be positioned within the first lumen of the sheath. The helical coil may be axially and rotatably movable relative to the sheath. The loop may have a first portion and a second portion. The second portion may extend radially outward from a distal portion of the sheath.

The medical device may include one or more of the following features. The second portion of the loop may be comprised of a resilient material. The first portion may be coupled to an external surface of the sheath. The sheath may define a second lumen. The first portion of the loop may be a wire disposed within the second lumen.

According to another aspect, a method may include delivering a medical system into a lumen to a treatment site. The medical system may include an insertion device having a working channel, a first medical device configured to be disposed within the working channel of the insertion device, a second medical device, and a third medical device. The second medical device may include a handle, a sheath extending from the handle and defining a lumen, a helical coil positioned within the lumen of the sheath, and a loop. The helical coil may be axially and rotatably movable relative to the sheath. A first portion of the loop may be coupled to the sheath. The second medical device may be configured to receive a second portion of the loop. The third medical device may be configured to be disposed within the working channel of the insertion device. The method may further include coupling the second portion of the loop to the treatment site using the first medical device, coupling the helical coil to a wall of the lumen, and resecting at least a portion of the treatment site using the third medical device.

Any of the examples described herein may have any of these features in any combination.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Although the treatment site is discussed herein as being in the subject's gastrointestinal tract, this disclosure is not so limited, as the treatment site may be any internal lumen, organ, cavity, or other tissue within the subject. Additionally, although endoscopes are referenced herein, it will be appreciated that the disclosure encompasses any medical devices having a working channel, or a lumen, extending from a proximal end to a distal end, such as ureteroscopes, duodenoscopes, gastroscopes, endoscopic ultrasonography ("EUS") scopes, colonoscopes, bronchoscopes, laparoscopes, arthroscopes, cystoscopes, aspiration scopes, sheaths, or catheters.

Embodiments of the disclosure may address one or more of the limitations in the art. The scope of the disclosure, however, is defined by the attached claims and not the ability to solve a specific problem. The present disclosure is drawn to devices, systems, and related methods, for a tissue lifting medical device, among other aspects.

Figure 1:
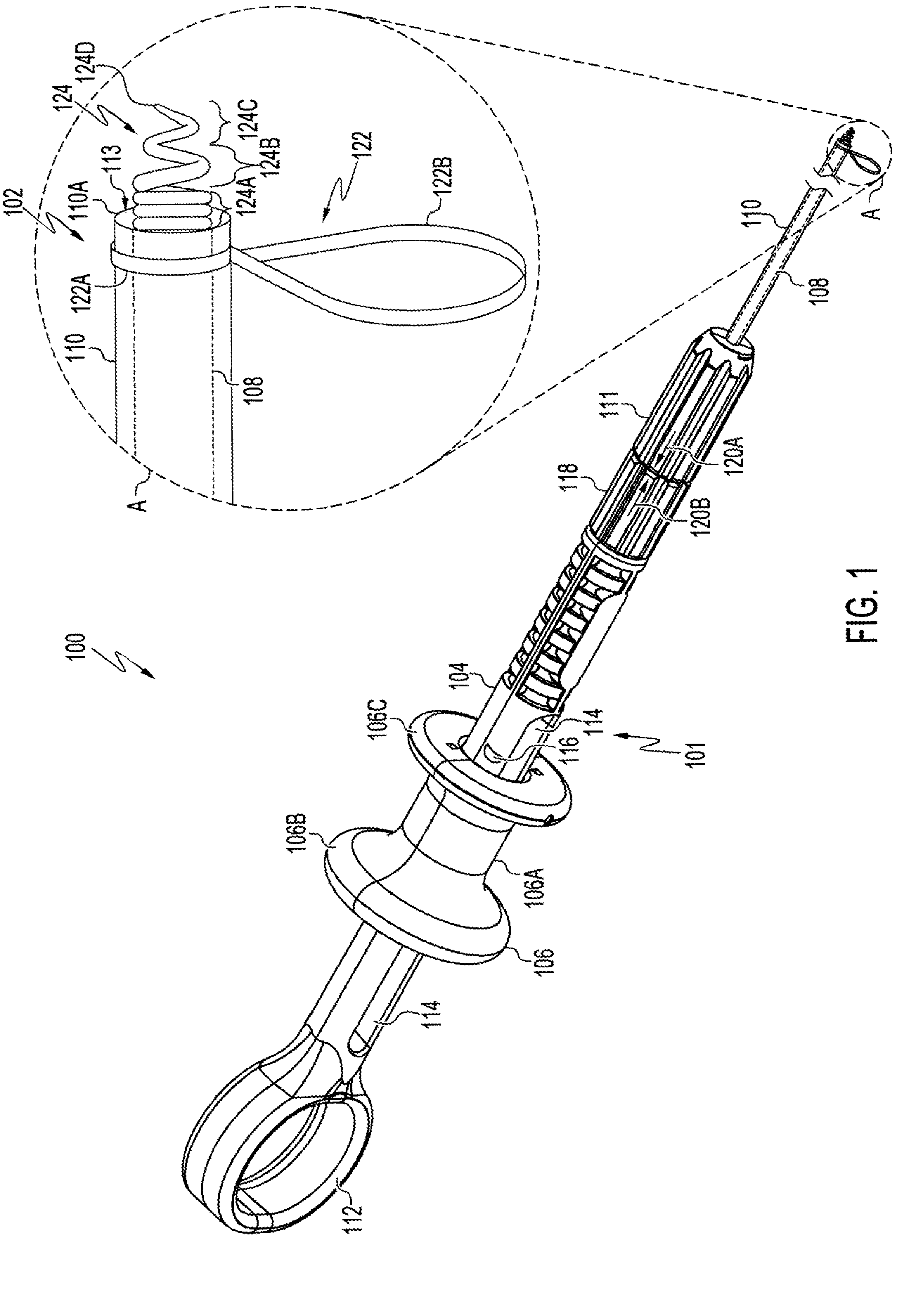
FIG. 1 illustrates a perspective view of a medical device, according to aspects of this disclosure.

FIG. 1 shows a perspective view of a medical device 100 having a handle 101 and a distal portion 102. One or more portions of handle 101 may be movable or manipulatable to control various aspects of distal portion 102. One or more portion(s) of distal portion 102 may be movable to facilitate, for example, coupling and/or de-coupling distal portion 102 to tissue. Distal portion 102 is shown in detail in circle A of FIG. 1.

Handle 101 may include a stationary body 104 and a first movable body, or a first actuator, 106. Movement of first movable body 106 relative to stationary body 104 may control the movement (e.g., extension or retraction) of a portion of distal portion 102. For example, one or more control elements 108 may be coupled to first movable body 106 and to a portion of distal portion 102, and thus first movable body 106 may control the movement (e.g., axial movement, such as extension or retraction) of one or more portions of distal portion 102. Control element(s) 108 may be comprised of any rigid or semi-rigid material, such as, for example, metals, polymers, metal-polymer composites, and the like. Control element(s) 108 may be formed by a coil, a braid, a tube, a sheath, etc. Control element(s) 108 may be coupled (e.g., directly or indirectly) or otherwise connected to first movable body 106 via, for example, an adhesive, a mechanical fit, a snap fit, a press fit, a weld, or any other coupling techniques commonly known in the art. In some embodiments, multiple control elements 108 are used. In such embodiments, each of the multiple control elements 108 are formed of the same or different materials and/or coupled or otherwise connected to first movable body 106 via the same or different coupling techniques.

An external sheath 110 may be coupled (e.g., directly or indirectly) or otherwise connected to a stationary distal handle portion 111 of handle 101, for example, an adhesive, a mechanical fit, a snap fit, a press fit, a weld, or any other coupling techniques commonly known in the art. Control element(s) 108 may be movable within external sheath 110, for example, within a lumen 113. A proximal portion of stationary body 104 may include a finger ring 112, for example, to receive the user's thumb.

First movable body 106 may at least partially surround a portion of stationary body 104, and a portion of first movable body 106 may at least partially extend into a handle slot 114. Handle slot 114 may extend longitudinally through at least a portion of stationary body 104 of handle 101. In some aspects, although not shown, handle 101 may include one or more biasing elements (e.g., one or more springs), for example, such that distal movement of first movable body 106 relative to stationary body 104 is biased proximally. In these aspects, when the user releases a distal pressure or force on first movable body 106, the one or more biasing elements may bias first movable body 106 proximally. Alternatively, the one or more biasing elements (e.g., one or more springs) may bias first movable body 106 distally. In these aspects, when the user releases a distal pressure or force on first movable body 106, the one or more biasing elements may bias first movable body 106 distally.

First movable body 106 may include one or more reduced diameter sections or grooves 106A, for example, between a proximal ridge 106B and a distal ridge 106C, which may help to facilitate the user's grip of first movable body 106. For example, the user may place first movable body 106 between two fingers such that the user's fingers are positioned within groove(s) 106A. Accordingly, movement of the user's fingers (i.e., relative to the user's thumb in finger ring 112) controls the position of first movable body 106 relative to stationary body 104, and thus the movement of control element(s) 108 and/or one or more portion(s) of distal portion 102.

Stationary body 104 may include one or more visual or physical indicator(s) 116. Indicator(s) 116 may physically or visually indicate the actuation, or extension, of one or more portion(s) of distal portion 102. For example, as first movable body 106 is advanced distally within handle slot 114 relative to stationary body 104, thus actuating one or more portion(s) of distal portion 102, first movable body 106 may have to overcome, for example, indicator(s) 116. Indicator (s) 116 may signal (e.g., via a tactile signal, via a visual signal, etc.) to the user that distal portion 102 has been actuated, or is in an extended position. Indicator(s) 116 may be on one side of handle 101 or on two opposing sides of handle 101 (e.g., opposite of indicator(s) 116 as shown in FIG. 1). Indicator(s) 116 may be a bump, a cantilevered protrusion, an indentation, a ridge, or any combination of the like. For example, indicator(s) 116 on one side of handle 101 may be a bump and indicator(s) 116 on an opposing side of handle 101 may be a cantilevered protrusion. Many other combinations are also contemplated. Additionally or alternatively, the user may utilize one or more markings on handle 101 (e.g., on stationary body 104 and/or first movable body 106) or other visual indicators to determine a status, position, actuation status, etc. of one or more portion(s) of distal portion 102.

Handle 101 may further include a second movable body, or a second actuator, 118. For example, movement of second movable body 118 may control the movement (e.g., rotation) of control element(s) 108, and thus one or more portion(s) of distal portion 102. For example, control element(s) 108 may be coupled to second movable body 118 via, for example, an adhesive, a mechanical fit, a snap fit, a press fit, a weld, or any other coupling techniques commonly known in the art.

Second movable body 118 may be positioned on a distal portion of handle 101. For example, second movable body 118 may be positioned distally on stationary body 104 relative to first movable body 106. Additionally or alternatively, second movable body 118 may be between stationary body 104 and distal handle portion 111 of handle 101. Distal handle portion 111 and/or second movable body 118 may include one or more ridges or indentations, for example, to facilitate a user's grip on handle 101.

Additionally or alternatively, distal handle portion 111 and/or second movable body 118 may include one or more visual or physical indicator(s) 120A and/or one or more visual or physical indicator(s) 120B. For example, indicator (s) 120A may be on distal handle portion 111 and indicator (s) 120B may be on second movable body 118. Indicator(s) 120A and/or indicator(s) 120B may comprise one or more of the characteristics of indicator(s) 116, described above.

Indicator(s) 120A and indicator(s) 120B may identify or signal the amount of and/or direction of the rotational movement a portion of distal portion 102, such as, for example, a helical coil 124. For example, a position between indicator(s) 120A on distal handle portion 111 and indicator (s) 120B on second movable body 118 may be indicative of the rotational movement of helical coil 124. For example, when indicator(s) 120A on distal handle portion 111 and indicator(s) 120B on second movable body 118 are aligned, helical coil 124 is not rotated. Similarly, when indicator(s) 120A on distal handle portion 111 and indicator(s) 120B on second movable body 118 are unaligned or misaligned, helical coil 124 is rotated.

Although not shown, handle 101 may include one or more locks such that first movable body 106 and/or second movable body 118 may be locked in position. For example, indicator(s) 116 may include one or more indentation(s) and/or protrusion(s) such that, when first movable body 106 is advanced distally over indicator(s) 116, first movable body 106 is locked in position and/or unable to be retracted proximally without again overcoming indicator(s) 116. Second movable body 118 may additionally or alternatively include a lock or securing mechanism (not shown), for example, to prevent rotational movement of second movable body 118. The lock or securing mechanism may include, for example, a ratcheting mechanism having a ratchet and a pawl, or any other lock or securing mechanism commonly known in the art. The lock or securing mechanism may alternatively or additionally include one or more biasing members, for example, to assist with controlling or more aspects of the handle (e.g., rotation, extension, retraction, etc.).

Distal portion 102, shown in more detail in circle A, may include a loop 122 and helical coil 124. At least a portion of loop 122 may be positioned proximal to a distalmost end 110A of external sheath 110. For example, a first portion 122A of loop 122 may at least partially extend around an external surface of external sheath 110. First portion 122A of loop 122 may be coupled to the external surface of external sheath 110 via, for example, an adhesive, a weld, a swage, a crimp, or any other coupling techniques commonly known in the art. Additionally or alternatively, external sheath 110 may include a groove (not shown) such that first portion 122A of loop 122 may be coupled to the external surface of external sheath 110 by, for example, a mechanical fit, a snap fit, a press fit, or any other coupling techniques commonly known in the art.

In some embodiments, first portion 122A of loop 122 may be comprised of one or more resilient material(s) such as, for example, elastic polymeric or rubber materials, or any other material commonly used in the art. In alternative embodiments, first portion 122A of loop 122 may be comprised of one or more rigid or semi-rigid material(s) such as, for example, metals, polymers, metal-polymer composites, and the like. In some embodiments, first portion 122A of loop 122 forms a continuous loop. In alternative embodiments (not shown), first portion 122A is C-shape, or forms a discontinuous loop. A cross-section of first portion 122A of loop 122 may be circular, ovular, elliptical, square, rectangular, hexagonal, or any other shape commonly used in the art.

A second portion 122B of loop 122 may extend radially outward from external sheath 110. In some embodiments, second portion 122B may form a continuous loop. Second portion 122B of loop 122 may be comprised of one or more resilient material(s) such as, for example, elastic polymeric or rubber materials, or any other material commonly used in the art. Second portion 122B may be comprised of the same material as first portion 122A or of a different material. For example, second portion 122B may be comprised of a first rubber material, and first portion may be comprised of a second rubber material, different from the first. Various other combinations of materials are also considered. A cross-section of second portion 122B may be circular, ovular, elliptical, square, rectangular, hexagonal, or any other shape commonly used in the art. In some configurations, second portion 122B may be larger than first portion 122A. For example, second portion 122B may have a circumference and/or a diameter greater than first portion 122A.

Helical coil 124 may be at least partially disposed within lumen 113 of external sheath 110. For example, in some configurations (e.g., when first movable body 106 is in a proximal or a proximalmost position), helical coil 124 may be disposed completely within the lumen 113 of external sheath 110, such that a distal tip 124D of helical coil 124 is proximal to distalmost end 110A of external sheath 110. In other configurations (e.g., when first movable body 106 is in a distal or distalmost position), at least a portion of helical coil 124 may be distal to distalmost end 110A of external sheath 110. Helical coil 124 may be comprised of a plurality of windings coupled (directly or indirectly) to a distal portion of control element(s) 108. Helical coil 124 may be coupled (directly or indirectly) to control element(s) 108 via, for example, a weld, an adhesive, a mechanical fit, a snap fit, a crimp, a swage, or other mechanisms commonly known in the art. In alternative configurations, helical coil 124 may be integrally formed with control element(s) 108. For example, a wire or coil forming helical coil 124 may also comprise or form control element(s) 108. In such a configuration, helical coil 124 may form a distalmost portion of control element(s) 108.

Helical coil 124 may include one to ten, or three to five, full helical turns. In some configurations, the plurality of windings forming helical coil 124 may be evenly spaced. In alternative configurations, a space between each of the plurality of windings forming helical coil 124 may vary. For example, in a proximal region 124A of helical coil 124, one or more adjacent windings may be spaced by a first distance. For example, the plurality of windings forming helical coil 124 in proximal region 124A may be in contact with one another. In a distal region 124C of helical coil 124, adjacent windings may be spaced by a second distance. In an intermediate region 124B, for example, between the proximal region 124A and the distal region 124C, adjacent windings may be spaced by a third distance. In some configurations, the second distance may be greater than the third distance, and the third distance may be greater than the first distance. Many other configurations are also contemplated. In further configurations, the second distance may be equal to the third distance such that the intermediate region 124B and distal region 124C are similarly spaced.

In further configurations, windings forming intermediate region 124B may have a non-constant pitch, resulting in a gradually increasing spacing. For example, the windings in the intermediate region 124B may transition from adjacent windings being in contact with one another in the proximal region 124A to the windings being spaced apart in the distal region 124C.

Distal tip 124D of helical coil 124 may be sharpened. Helical coil 124 may be formed from a solid round wire or a plurality of wire(s). In some configurations, helical coil 124 may be configured to have a diameter less than an inner diameter of external sheath 110. For example, helical coil 124 may have an outer cross-sectional diameter between 0.002 inches and 0.200 inches, for example between 0.005 inches and 0.020 inches. Helical coil 124 may have an inner cross-sectional diameter between 0.001 inches and 0.190 inches, for example, between 0.002 inches and 0.015 inches. In some configurations, the wire(s) forming helical coil 124 may have a cross-sectional diameter greater than or equal to a wire or a plurality of wires forming control element(s) 108. In alternative configurations, the wire(s) forming helical coil 124 may have a cross-sectional diameter less than a wire or a plurality of wires forming control element(s) 108. For example, the wire(s) forming helical coil 124 may have a cross-sectional diameter between 0.0005 inches and 0.100 inches, for example, between 0.005 inches and 0.015 inches.

Although not shown, helical coil 124 may include one or more markers, such as, for example, radiopaque marker(s), ultrasonic marker(s), etc., to assist the user with determining a status, position, actuation status, etc. of helical coil 124. For example, a winding or portion of a winding in proximal region 124A and/or intermediate region 124B may include a visual marker to signal to the user how deep the helical coil 124 is within a tissue, or how many windings of helical coil 124 has been inserted into the tissue.

Referring still to FIG. 1, control element(s) 108 may extend from one or more portions of handle 101 of medical device 100 (e.g., from a distal portion of first movable body 106) to one or more portions of distal portion 102. Control element(s) 108 may each be formed by a wire, a coil, a tube, etc. Additionally, external sheath 110 may extend from one or more portions of handle 101 (e.g., from a distal portion of distal handle portion 111) to one or more portions of distal portion 102. External sheath 110 may be formed by a coil, a braid, a tube, a sheath, etc., and lumen 113 may extend longitudinally within external sheath 110, for example, to receive control element(s) 108. In these aspects, control element(s) 108 may be radially within external sheath 110. For example, control element(s) 108 may be longitudinally and/or rotatably movable relative to external sheath 110 and disposed within lumen 113 of external sheath 110.

Figure 2A:
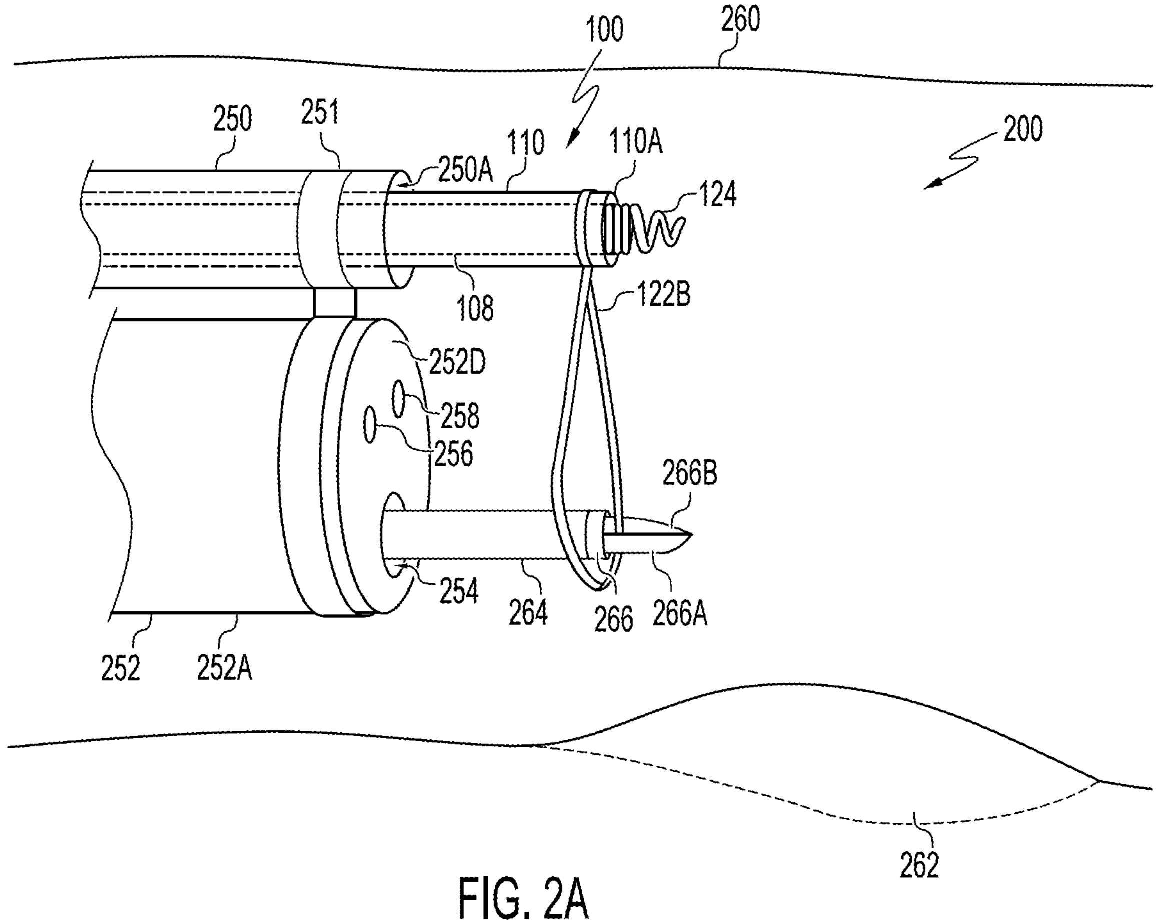
FIGS. 2A-2C illustrate perspective views of a distal portion of an exemplary medical system at various states during operation, according to aspects of this disclosure.

Referring now to FIG. 2A, a medical system 200 is shown. Medical system 200 includes medical device 100 (described above and shown in FIG. 1). As shown, in some embodiments, medical system 200 includes an endoscope 252 and a sheath 250. Sheath 250 may be coupled to an external surface of an endoscope 252, for example, by a coupler 251, and may assist with encapsulating one or more portions of medical device 100 and/or or coupling medical device 100 to endoscope 252. For example, medical device 100 may be disposed within a lumen 250A of sheath 250. In alternative configurations (not shown), medical device 100 may extend externally to endoscope 252 (e.g., along an external surface of endoscope 252), for example, without the use of sheath 250.

In some aspects, one or more portions of external sheath 110 may be coupled to one or more portions of endoscope 252 Alternatively, external sheath 110 of medical device 100 may extend through a lumen of endoscope 252, for example through a working channel 254 or through a second, separate lumen (not shown). Alternatively, one or more portions of system 200 may be inserted via and/or surrounded via an insertion sheath (not shown), for example, surrounding sheath 250 and endoscope 252. Additionally, FIG. 3 illustrates an exemplary method, or process, 300 that one or more users may perform with any of the medical systems, devices, or portions of systems discussed herein, for example, medical system 200.

Although not shown, one or more portions of endoscope 252 (e.g., a distal portion 252A) may be deflectable, for example, via one or more knobs, levers, buttons, or other controls on a proximal handle (not shown) of endoscope 252. In these aspects, distal portion 252A of endoscope 252 may be maneuvered while being delivered through a lumen, to the treatment site and/or positioned relative to the treatment site, for example, in a retroflex position, which may be used when the treatment site is in the subject's esophagus, stomach, duodenum, colon, or other portion of the gastrointestinal tract. Accordingly, at least portions of medical device 100 may be flexible or semi-flexible, for example, in order to be maneuvered along with endoscope 252. Additionally, a distal face 252D of endoscope 252 may include one or more visualization device(s) 256 (e.g., one or more cameras, light emitting diodes (LEDs), one or more image sensors, endoscope viewing elements, optical assemblies, including one or more image sensors, and one or more lenses, etc.). Distal face 252D of endoscope 252 may additionally or alternatively include one or more opening(s) 258 configured to supply a liquid, a gas, and/or suction to the subject.

Figure 3:
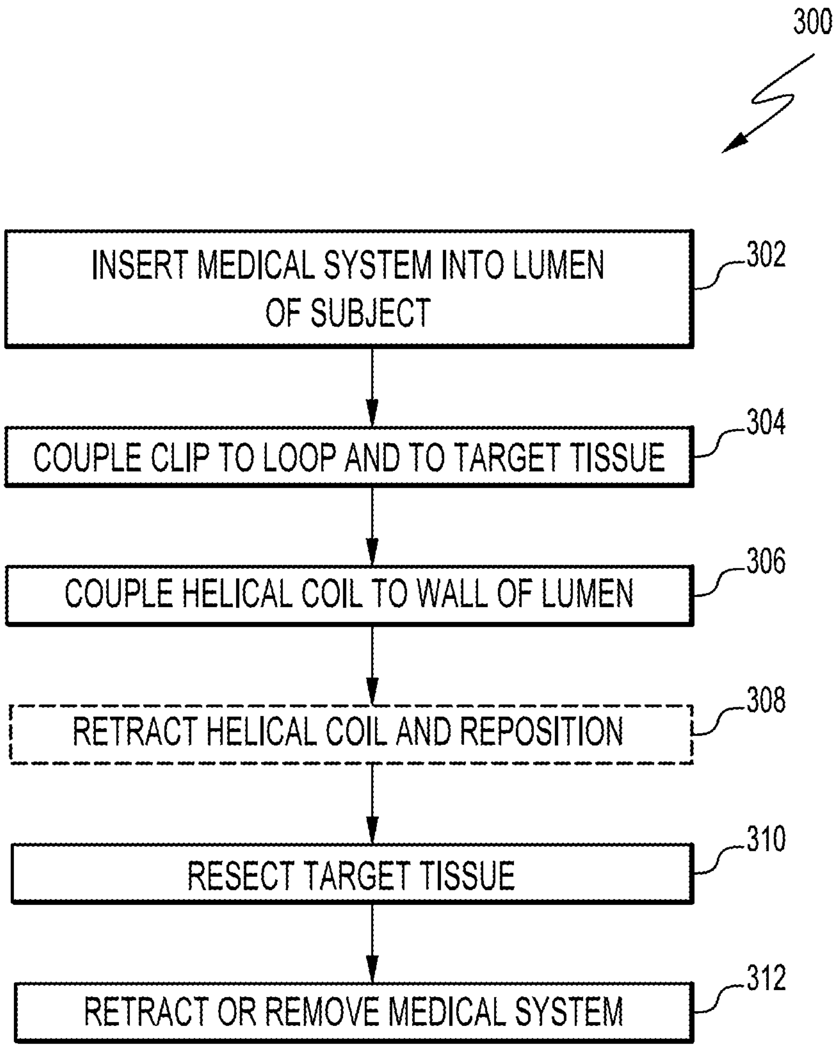
FIG. 3 is a flow diagram of an exemplary method, according to aspects of this disclosure.

In referring to FIGS. 2A and 3, in a step 302, medical system 200 (e.g., a distal portion of medical system 200) may be inserted into a lumen 260 of the subject, for example, through a natural orifice or an incision. Medical system 200 may further include a device 264 having a clip 266, and medical system 200 may also include a cutting tool 268. Device 264 and cutting tool 268 are described in further detail below. Each of device 264 and cutting tool 268 may be configured to be disposed within working channel 254 of endoscope 252. For example, device 264 may be inserted into working channel 254 of endoscope 252. Before, during, or after device 264 is removed from working channel 254, cutting tool 268 may be inserted into working channel 254. Clip 266 may be any clip commonly used in the art, for example, clip 266 may be a hemoclip or an endoclip. Clip 266 may include a first leg 266A and a second leg 266B.

Once medical system 200 is in a desired position within lumen 260, for example, near or adjacent to a treatment site 262, device 264 may be inserted through working channel 254 of endoscope 252, such that a distal portion of device 264 is distal to distal face 252D of endoscope 252. A portion of second portion 122B of loop 122 may be positioned within clip 266, for example, between first leg 266A and second leg 266B. To position second portion 122B of loop 122 between first leg 266A and second leg 266B, medical device 100 may be pushed, pulled, or rotated within sheath 250. Additionally or alternatively, endoscope 252 may be pushed, pulled, rotated, or deflected within lumen 260, and/or device 264 may be pushed, pulled, or rotated within working channel 254 of endoscope 252.

Before or after second portion 122B of loop 122 is positioned within clip 266, at least a portion of helical coil 124 may be actuated, or extended distally to distalmost end 110A of external sheath 110. For example, first movable body 106 (shown in FIG. 1) may be actuated, extended, or pushed distally within handle slot 114 of handle 101, such that control element(s) 108 is actuated, extended, or pushed distally and, accordingly, such that at least a portion of helical coil 124 is distal to the distalmost end 110A of external sheath 110.

In some configurations, endoscope 252 may be oriented such that working channel 254 is positioned closer to second portion 122B, for example, to assist with positioning second portion 122B between first leg 266A and second leg 266B. For example, endoscope 22 may be orientated such that working channel 254 is in a 6 o'clock position relative to visualization device(s) 256 and/or opening(s) 258. In alternative configurations, endoscope 252 is oriented such that working channel 254 is in a 3 o'clock, 9 o'clock, or 12 o'clock position relative to visualization device(s) 256 and/or opening(s) 258. Many other configurations are also contemplated, for example, to assist with positioning second portion 122B between first leg 266A and second leg 266B of clip 266.

Figure 2B:
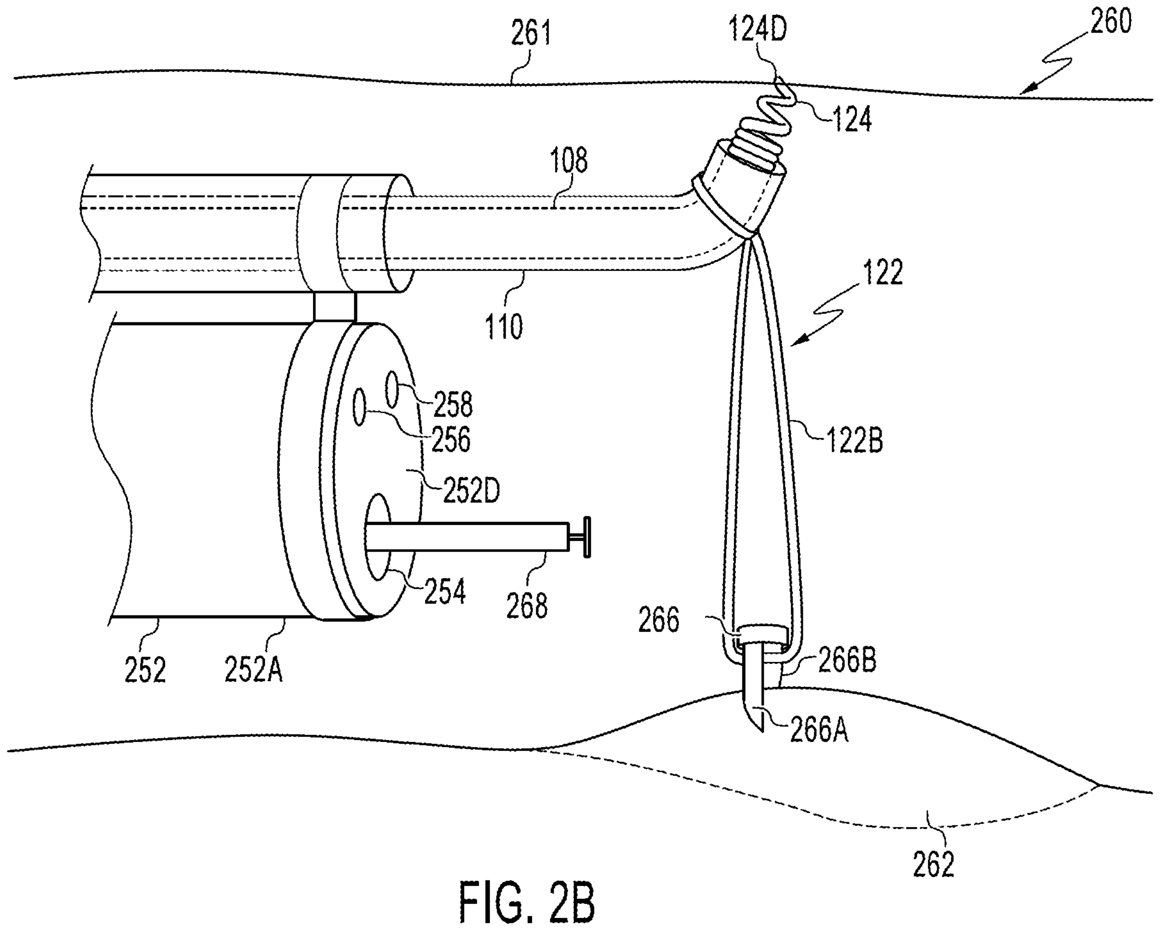

Referring now to FIGS. 2B and 3, in a step 304, clip 266 may be coupled, or anchored, to treatment site 262. Clip 266 is subsequently released from the remainder of device 264. Accordingly, second portion 122B of loop 122 may be anchored to treatment site 262, for example, between clip 266 and treatment site 262. For example, second portion 122B may be anchored between first leg 266A and second leg 266B of clip 266 and treatment site 262. Once clip 266 is anchored to treatment site 262, endoscope 252 may be maneuvered to position helical coil 124 of medical device 100 in contact with a wall of lumen 260, for example, opposite of or across lumen 260 from treatment site 262. Endoscope 252 may be maneuvered by, for example, deflecting distal portion 252A, advancing endoscope 252 distally, and/or retracting endoscope 252 proximally. Additionally or alternatively, visualization device(s) 256 may be use to maneuver and/or reposition endoscope 252.

Once helical coil 124 is in contact with a wall 261 of lumen 260, control element(s) 108 and, thus, helical coil 124 may be rotated in a first direction (e.g., clockwise or counterclockwise). Control element(s) 108 may be rotated by, for example, rotating second movable body 118 in the first direction. Accordingly, as helical coil 124 is rotated in the first direction, distal tip 124D of helical coil 124 may pierce wall 261 of lumen 260. Continued rotation of helical coil 124 in the first direction may cause the distal tip 124D to be driven deeper into the tissue wall, for example, in a corkscrew manner. In such a way, helical coil 124 may be advanced distally from a distalmost end of external sheath 110.

Accordingly, as shown in FIG. 2B and described in FIG. 3, in a step 306, helical coil 124 may be anchored, or coupled, to wall 261 of lumen 260, for example, opposite of or across lumen 260 from treatment site 262. One or more windings of helical coil 124 may be embedded into wall 261 of lumen 260, for example, to ensure helical coil 124 is securely fastened, coupled, or attached to wall 261 of lumen 260. Visual markers described previously in FIG. 1 may be used to determine, for example, how many windings are or what portion of helical coil 124 is within wall 261 of lumen 260.

With helical coil 124 anchored to wall 261 of lumen 260 and second portion 122B of loop 122 anchored to treatment site 262, second portion 122B of loop 122 may be subjected to tension, and tissue of treatment site 262 may be lifted or similarly tensioned. Although not shown, an injection needle may be introduced through working channel 254 of endoscope 252. The injection needle may be used to inject a fluid in the tissue of treatment site 262, for example, to assist with lifting tissue of treatment site 262. In such a way, tissue of treatment site 262 may be lifted by both the fluid introduced via the injection needle and the tension from second portion 122B of loop 122.

Figure 2C:
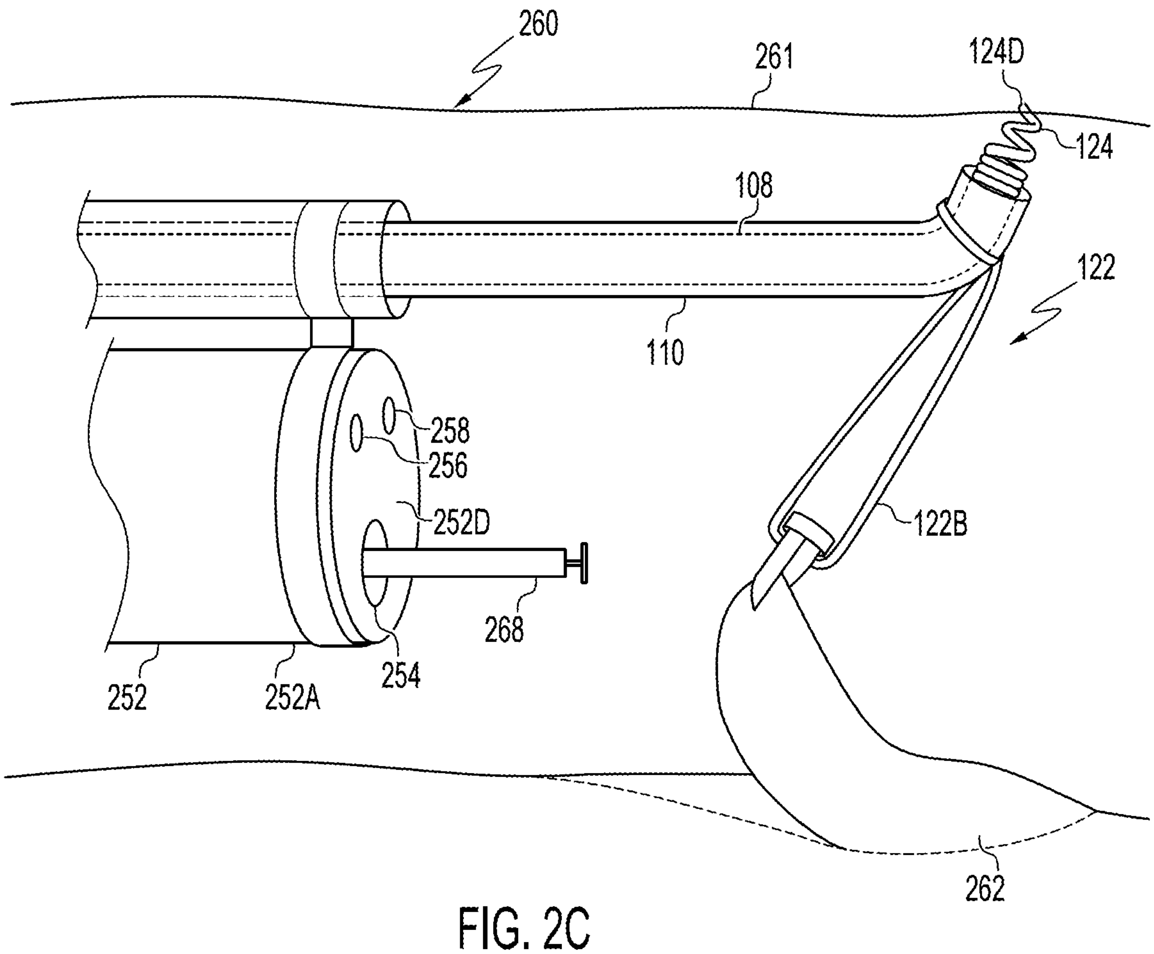

As shown in FIGS. 2B and 2C, cutting tool 268, for example, a knife, scissors, a blade, an electrocautery knife, or any other resection or cutting device may be introduced through working channel 254 of endoscope 252. Cutting tool 268 may be used to cut, or resect, tissue from treatment site 262. In some embodiments, cutting tool 268 may include a lumen, for example, to deliver fluid. Similar to the injection needle described above, cutting tool 268 may thus be configured to inject a fluid in the tissue of treatment site 262, for example, to assist with lifting tissue of treatment site 262 before cutting the tissue. In addition to the fluid injected in the tissue of treatment site 262, if any, the tension of second portion 122B may cause the resected tissue of treatment site 262 to lift, for example, as treatment site 262 is cut or resected. Accordingly, as the resected portion of treatment site 262 is lifted, the tension of second portion 122B may decrease.

As shown in FIG. 2C and in an optional step 308, helical coil 124 may be repositioned. Accordingly, second portion 122B of loop 122 may be re-tensioned, for example, by repositioning helical coil 124. To reposition helical coil 124 and, subsequently, to re-tension second portion 122B, helical coil 124 may be rotated in a second direction (e.g., counterclockwise or clockwise), opposite the first direction. To rotate helical coil 124 in the second direction, second movable body 118 may be rotated in the second direction and, thus, control element(s) 108 coupled to helical coil 124 may be rotated in the second direction. Accordingly, helical coil 124 may be uncoupled, or withdrawn, from wall 261 of lumen 260. As helical coil 124 is uncoupled or withdrawn, helical coil 124 may be retracted proximally within external sheath 110. Once uncoupled or withdrawn from wall 261 of lumen 260, helical coil 124 may be repositioned, for example, distally to treatment site 262, such that second portion 122B of loop 122 is, once again, under tension. Cutting tool 268 may then be used to continue to cut, or resect, tissue from treatment site 262 in a step 310. Optional step 308 and/or step 310 may be repeated such that helical coil 124 may be repositioned and/or second portion 122B may be re-tensioned numerous times, for example, until treatment site 262 is resected to the desired amount. Additionally or alternatively, optional step 308 may be performed before resecting tissue from treatment site 262, for example, if there is not the desired tension in second portion 122B or otherwise improper positioning of helical coil 124 after helical coil 124 is coupled to wall 261 of lumen 260.

Once tissue from treatment site 262 is appropriately resected, in a step 312, one or more portions of medical system 200 may be retracted or removed proximally. For example, medical device 100, cutting tool 268, and/or endoscope 252 may be retracted or removed proximally. Accordingly, medical device 100 and/or the resected tissue from treatment site 262 coupled to clip 266 may then be removed from lumen 260. In some embodiments, cutting tool 268 may be used to detach second portion 122B of loop 122 from medical device 100, such that, for example, resected tissue from treatment site 262 may be passed naturally by the subject or removed through working channel 254 of endoscope 252, for example, by applying suction. Although not shown, resected tissue from treatment site 262 may be removed through working channel 254 of endoscope 252, for example, by using one or more graspers, nets, cages, suction, or any other device(s) or method(s) commonly used in the art to remove objects from a subject.

Figure 4:
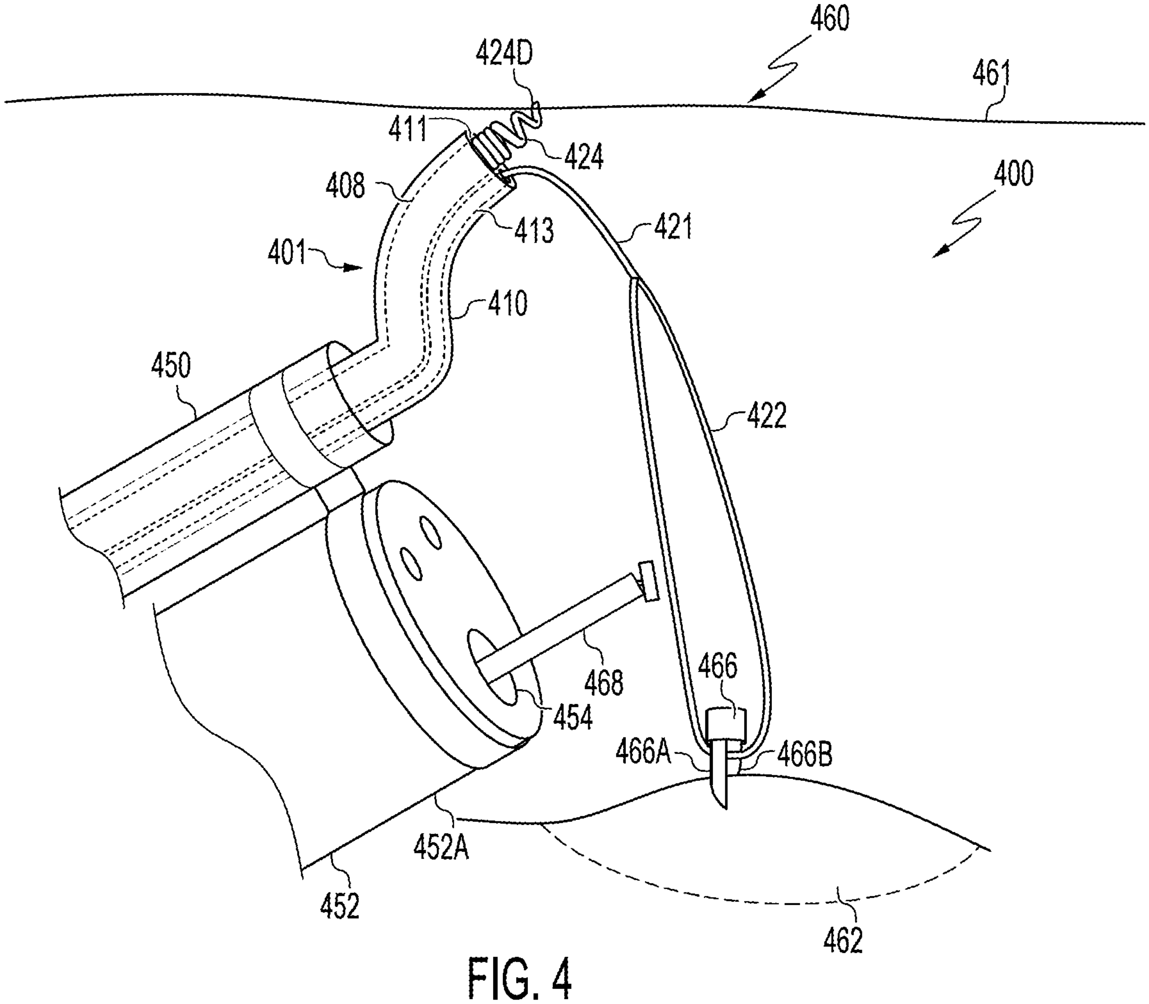
FIG. 4 illustrates a perspective view of a distal portion of an alternative embodiment of a medical system, according to aspects of this disclosure.

FIG. 4 illustrates an alternative embodiment of a medical system 400. Medical system 400 may include a medical device 401, an endoscope 452, and a sheath 450. Medical system 400 may comprise any of the characteristics of medical system 200, except as described below. For example, sheath 450 may comprise any of the characteristics of sheath 250. Endoscope 452 may comprise any of the characteristics of endoscope 252, and medical device 401 may comprise any of the characteristics of medical device 100, except as described below. Additionally, medical system 400 may be used to perform one or more steps of method 300, except as described below.

In this embodiment, medical device 401 includes one or more control elements 408, an external sheath 410, a helical coil 424, and a wire 421 forming a loop 422. Control element(s) 408 and/or helical coil 424 may have any of the characteristics of control element(s) 108 and helical coil 124 of medical device 100, respectively. External sheath 410 may have any of the characteristics of external sheath 110 of medical device 100, except as described below.

External sheath 410 may include a first lumen 411 extending longitudinally along a length of external sheath 410, and the first lumen 411 may receive control element(s) 408 and/or at least one or more portions of helical coil 424. External sheath 410 may also include a second lumen 413 extending longitudinally along a length of external sheath 410, for example, substantially parallel to first lumen 411. Second lumen 413 of external sheath 410 may be configured to receive a proximal portion of wire 421 and/or loop 422. For example, wire 421 and, thus, loop 422 may be at least partially disposed within second lumen 413 of external sheath 410 in a first, or retracted configuration (not shown). Wire 421 and loop 422 may be longitudinally and/or rotatably movable relative to second lumen 413.

Although not shown, a proximal portion of wire 421 may be coupled to an actuator in a handle of medical device 401. The actuator (not shown) may be configured to control the longitudinal and/or rotational movement of wire 421, and thus loop 422. In alternative configurations, a proximal portion of wire 421 may extend longitudinally through second lumen 413 and exit the handle, for example, via a port or an opening (not shown).

Referring still to FIG. 4, wire 421 and/or loop 422 may be comprised of a single wire or may be comprised of a plurality of wires grouped together, for example, to form a cable. Wire 421 may alternatively be comprised of one or more thread(s), suture(s), cord(s), or any combination thereof. Wire 421 may be comprised of one or more resilient, flexible, and/or semi-rigid material(s) such as, for example, metals, polymers, metal-polymer composites, and the like. Loop 422 may be comprised of one or more resilient materials, such as, for example, elastic polymeric or rubber materials, or any other material commonly used in the art. Loop 422 may be formed similarly to second portion 122B of loop 122, shown in FIG. 1 and described above. In some configurations, wire 421 and loop 422 may be separate components coupled via, for example, an adhesive, a crimp, a swage, a knot, a mechanical fit, or other mechanism commonly known in the art. In some configurations, wire 421 and loop 422 may be integrally formed.

Medical system 400 may be used similarly to medical system 200. For example, medical system 400 (e.g., a distal portion of medical system 400) may be inserted into a lumen 460 of the subject, for example, through a natural orifice or an incision. A clip 466 may be used to couple, or anchor, a portion of loop 422 to a treatment site 462. For example, clip 466 may further comprise a first leg 466A and a second leg 466B. A portion of loop 422 may be positioned between first leg 466A, second leg 466B, and treatment site 462, such that loop 422 is anchored to treatment site 462 via clip 466. Endoscope 452 may be maneuvered by, for example, rotating endoscope 452, deflecting a distal portion 452A, advancing endoscope 452 distally, and/or retracting endoscope 452 proximally to direct clip 466 to treatment site 462. Endoscope 452 may be similarly maneuvered such that helical coil 424 is in contact with a wall 461 of lumen 460, for example, opposite of or across lumen 460 from treatment site 462.

Once helical coil 424 is in contact with wall 461 of lumen 460, control element(s) 408 and, thus, helical coil 424 may be rotated in a first direction. Accordingly, as helical coil 424 is rotated in the first direction, sharpened distal tip 424D of helical coil 424 may pierce wall 461 of lumen 460. Continued rotation of helical coil 424 in the first direction may cause sharpened distal tip 424D to be driven deeper into the tissue wall, for example, in a corkscrew manner. In such a way, helical coil 424 may be advanced distally from a distalmost end of external sheath 410. Accordingly, helical coil 424 may be anchored, or coupled, to wall 461 of lumen 460, for example, opposite of or across lumen 460 from treatment site 462. If necessary, helical coil 424 may be repositioned one or more times, as discussed above.

With helical coil 424 anchored to wall 461 of lumen 460 and loop 422 anchored to the target tissue by clip 466, loop 422 may be tensioned by, for example, pulling or retracting wire 421 proximally. As tension is introduced to loop 422, the tissue of treatment site 462 may be tensioned and/or lifted. Additionally or alternatively, helical coil 424 may be repositioned within lumen 460, for example, to tension loop 422.

A cutting tool 468 may be introduced via a lumen 454 of endoscope 452. Cutting tool 468 may be used to cut, or resect, tissue from treatment site 462. The tension of loop 422 may cause the resected portion of treatment site 462 to lift. Accordingly, as the resected portion of treatment site 462 is lifted, the tension of loop 422 may decrease. Loop 422 may be optionally re-tensioned by, for example, pulling or retracting wire 421 proximally and/or repositioning helical coil 424 within lumen 460, as discussed above.

Helical coil 424 may be removed or repositioned by, for example, rotating helical coil 424 in a second direction, opposite the first direction, to withdraw helical coil 424 from wall 461 of lumen 460. Once withdrawn from wall 461 of lumen 460, helical coil may be removed or repositioned, for example, distally from treatment site 462.

Once tissue from treatment site 462 is appropriately resected, one or more portions of medical system 400 may be retracted or removed proximally. For example, medical device 401, cutting tool 468, and/or endoscope 452 may be retracted or removed proximally. Accordingly, medical device 100 and/or the resected tissue from treatment site 462 coupled to clip 466 may then be removed from lumen 460. In some embodiments, cutting tool 468 may be used to detach second portion 422B of loop 422 from medical device 401, such that, for example, resected tissue from treatment site 462 may be passed naturally by the subject or removed through lumen 454 of endoscope 452, for example, by applying suction. Although not shown, resected tissue from treatment site 462 may be removed through lumen 454 of endoscope 452, for example, by using one or more graspers, nets, cages, suction, or any other device(s) or method(s) commonly used in the art to remove objects from a subject.

Figure 5C:
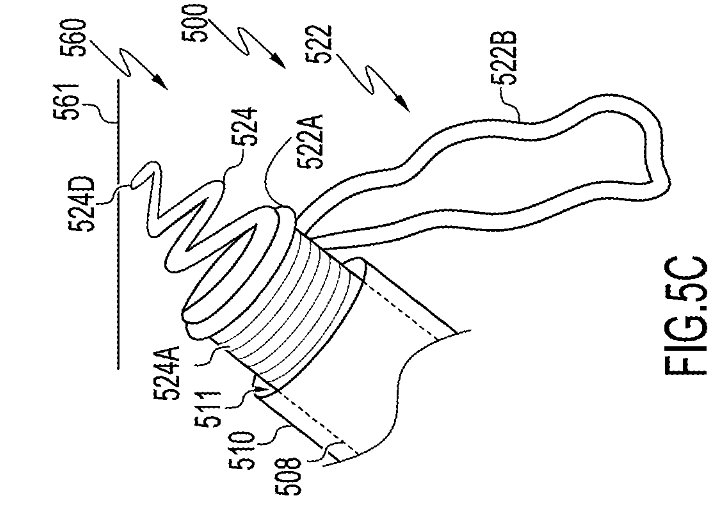
FIGS. 5A-5C illustrate perspective views of a distal portion of an alternative embodiment of a medical device, according to aspects of this disclosure.
Figure 5B:
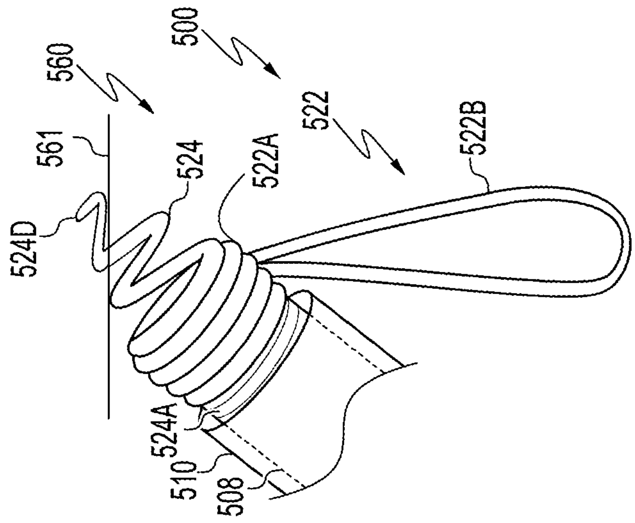
Figure 5A:
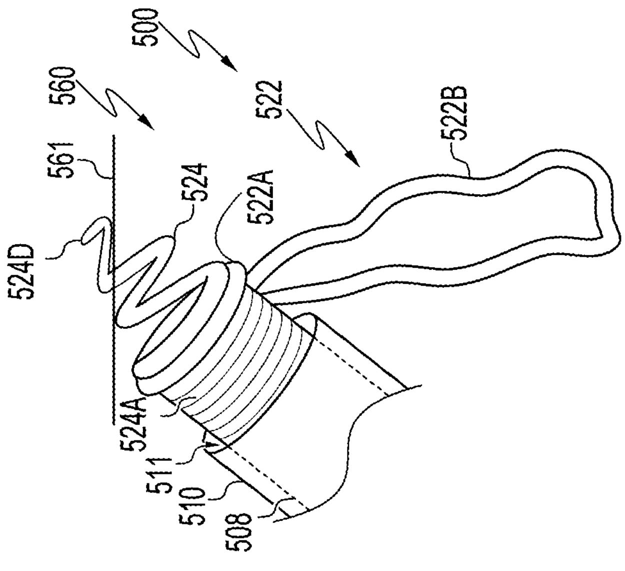

FIGS. 5A-5C illustrate perspective views of a distal portion of an alternative embodiment of a medical device 500. For example, FIG. 5A illustrates medical device 500 in a first configuration. FIG. 5B illustrates medical device 500 in a second configuration, and FIG. 5C illustrates medical device 500 in a third configuration. Medical device 500 may comprise any of the characteristics of medical device 100 and/or medical device 401, except as described below.

Medical device 500 may include one or more control elements 508, an external sheath 510, a helical coil 524, and a loop 522. Control element(s) 508 may have any of the characteristics of control element(s) 108 and/or control element(s) 408. External sheath 510 may have any of the characteristics of external sheath 110 and/or external sheath 410. For example, external sheath 510 may include an internal lumen 511. At least a portion of control element(s) 508 and/or helical coil 524 may be disposed within internal lumen 511, for example, in a retracted configuration (not shown). Helical coil 524 may have any of the characteristics of helical coil 124 and/or helical coil 424. Loop 522 may have any of the characteristics of loop 122 and/or loop 422, except as described below.

Loop 522 may be positioned proximal to helical coil 524, for example, on an external surface of a proximal portion 524A of helical coil 524 and/or an external surface of control element(s) 508. A first portion 522A of loop 522 may at least partially extend around the external surface of proximal portion 524A of helical coil 524 or control element(s) 508. First portion 522A of loop 522 may be coupled to the external surface of helical coil 524 or control element(s) 508 via, for example, an adhesive, a mechanical fit, a snap fit, a press fit, a weld, a swage, a crimp, or any other coupling techniques commonly known in the art.

A second portion 522B of loop 522 may extend radially outward from first portion 522A of loop 522. Each of first portion 522A and second portion 522B of loop 522 may be comprised of one or more resilient material(s) such as, for example, elastic polymeric or rubber materials, or any other material commonly used in the art. First portion 522A and second portion 522B may be comprised of the same material or of a different material. In alternative embodiments, first portion 522A may be comprised of one or more rigid or semi-rigid material(s) such as, for example, metals, polymers, metal-polymer composites, and the like. Additionally or alternatively, first portion 522A and second portion 522B may be coupled via, for example, an adhesive, a crimp, a swage, a knot, a mechanical fit, or other coupling techniques commonly known in the art. In some configurations, first portion 522A and second portion 522B may be integrally formed.

Medical device 500 may be used similarly to medical device 100 and/or medical device 401, except as described below. For example, medical device 500 may be used with medical system 200 or medical system 400. Medical device 500 may be inserted into a lumen 560 of the subject, for example, through a natural orifice or an incision. A clip (not shown) may be used to couple, or anchor, second portion 522B of loop 422 to a target tissue (not shown).

As shown in FIG. 5A, helical coil 524 may be coupled, or anchored, to a wall 561 of lumen 560. For example, helical coil 524 may be coupled, or anchored to wall 561 of lumen 560 opposite of the target tissue. Similar to helical coil 124 of FIGS. 1 and 2A-2C and helical coil 424 of FIG. 4, helical coil 524 may be rotated in a first direction such that a sharpened distal tip 524D may pierce wall 561 of lumen 560. Continued rotation of helical coil 524 in the first direction may cause sharpened distal tip 524D to be driven deeper into the tissue wall, for example, in a corkscrew manner. Accordingly, helical coil 524 may be coupled to wall 561 of lumen 560.

With helical coil anchored to wall 561 of lumen 560 and loop 522 anchored to the target tissue by the clip (not shown), second portion 522B of loop 522 may be loose (e.g., not subjected to any tension) or subjected to a first tension. To increase tension of second portion 522B, for example, to tension second portion 522B as target tissue (not shown) is resected or cut, control element(s) 508, and thus helical coil 524 may be rotated in a first direction, for example, clockwise or counterclockwise. As shown in FIG. 5B, rotating control element(s) 508 in the first direction may cause second portion 522B of loop 522 to partially or completely wrap around the external surface of proximal portion 524A of helical coil 524 or control element(s) 508. Accordingly, as second portion 522B is wrapped around control element(s) 508, second portion 522B may be subjected to a second, greater tension. Additionally or alternatively, helical coil 524 may be repositioned in wall 561 of lumen 560 to increase or otherwise adjust tension within second portion 522B. For example, helical coil 524 may be coupled to a portion of the wall that is distal to the target tissue.

To remove tension from second portion 522B, control element(s) 508 and, thus, helical coil 524, may be rotated in a second direction, opposite the first direction, for example, counterclockwise or clockwise. As control element(s) 508 is rotated in the second direction, second portion 522B may be unwound from control element(s) 508 and thus tension may decrease within second portion 522B and/or the target tissue may be lowered. Additionally or alternatively, helical coil 524 may be rotated in the second direction, opposite the first direction, such that helical coil 524 is uncoupled from wall 561 of lumen 560, as shown in FIG. 5C. Helical coil 524 may additionally or alternatively be repositioned in wall 561 of lumen 560 to decrease tension within second portion 522B. For example, helical coil 524 may be coupled to a portion of the wall that is proximal of the target tissue.

In some configurations, control element(s) 508 may be independently movable relative to helical coil 524. For example, proximal portion 524A of helical coil 524 may be coupled to a separate actuator within the handle (not shown). In such a way, helical coil 524 may be rotated independently from control element(s) 508. Accordingly, as helical coil 524 is coupled to wall 561 of lumen 560, tension is neither introduced nor removed from second portion 522B of loop 522. Similarly, as control element 508 is rotated to tension or loosen second portion 522B, helical coil 524 may remain coupled to wall 561 of lumen 560.

In further alternative configurations (not shown), medical device 500 includes two or more control elements 508. For example, medical device 500 may include a first control element that is rotatable to control helical coil 524, and a second control element that is rotatable to control the tension of loop 522. Accordingly, the second control element may be disposed within the first control element, for example, through a lumen extending through the first control element. In such a manner, helical coil 524 may be rotated independently from control element(s) 508. Accordingly, as helical coil 524 is coupled to wall 561 of lumen 560, tension is neither introduced nor removed from second portion 522B of loop 522. Similarly, as control element(s) 508 is rotated to tension or loosen second portion 522B, helical coil 524 may remain coupled to wall 561 of lumen 560.

Each embodiment discussed herein may enable the user to apply tension to tissue, for example, in order to lift tissue such that the tissue may be more easily cut, resected, removed, or otherwise treated. Each embodiment may help to decrease procedure time, a likelihood of patient injury, and/or a likelihood of other procedural complications.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

We claim:

1. A medical system, comprising:
an insertion device having a working channel;
a first medical device having:
  a handle;
  a sheath extending from the handle and defining a lumen;
  a helical coil, wherein the helical coil is axially and rotatably movable relative to the sheath; and
  a loop, wherein a first portion of the loop is coupled to the sheath and a second portion of the loop extends radially away from the sheath; and
a second medical device configured to be disposed within the working channel of the insertion device, wherein the second medical device is configured to receive the second portion of the loop, and wherein the second medical device is configured to couple the second portion of the loop to a portion of a treatment site, wherein the second medical device includes a clip.

2. The medical system of claim 1, wherein a distal end of the helical coil is sharpened.

3. The medical system of claim 1, wherein the handle includes a stationary body, a first actuator, and a second actuator, wherein the first actuator controls axial movement of the helical coil, wherein the second actuator controls rotational movement of the helical coil, and wherein a control element couples the first actuator and the second actuator to the helical coil.

4. The medical system of claim 3, wherein the stationary body includes a first indicator to identify the axial movement of the helical coil, and wherein the second actuator includes a second indicator to identify the rotational movement of the helical coil.

5. The medical system of claim 1, wherein rotation of the helical coil in a first direction is configured to couple the helical coil to a tissue wall.

6. The medical system of claim 5, wherein the tissue wall is opposite of the treatment site.

7. The medical system of claim 5, wherein rotation of the helical coil in a second direction is configured to uncouple the helical coil from the tissue wall.

8. The medical system of claim 1, wherein the helical coil includes a plurality of windings, wherein adjacent windings of a first portion of the plurality of windings are spaced by a first distance, wherein adjacent windings of a second portion of the plurality of windings are spaced by a second distance, and wherein adjacent windings of a third portion of the plurality of windings are spaced by a third distance.

9. The medical system of claim 8, wherein the third distance is greater than the second distance, and wherein the second distance is greater than the first distance.

10. The medical system of claim 1, further comprising a coupler, wherein the coupler couples the first medical device to an external surface of the insertion device.

11. The medical system of claim 1, wherein the second portion of the loop is comprised of a resilient material.

12. The medical system of claim 1, further including a third medical device configured to be disposed within the working channel of the insertion device, wherein the third medical device is configured to cut tissue.

13. The medical system of claim 1, wherein the insertion device is a scope, wherein a distal portion of the scope is deflectable.

14. The medical system of claim 1, wherein the insertion device includes one or more visualization devices.

* * * * *